United States Patent [19]

Blok et al.

[11] Patent Number: 5,783,705

[45] Date of Patent: Jul. 21, 1998

[54] PROCESS OF PREPARING ALKALI METAL SALYS OF HYDROPHOBIC SULFONAMIDES

[75] Inventors: Natalie Blok; Chengde Wu; Karin Keller. all of Houston; Timothy P. Kogan. Sugarland, all of Tex.

[73] Assignee: Texas Biotechnology Corporation. Houston, Tex.

[21] Appl. No.: 847,797

[22] Filed: Apr. 28, 1997

[51] Int. Cl.$^6$ ............ C07D 261/06; C07D 261/14; C07D 261/04

[52] U.S. Cl. ............ 548/247; 548/240; 548/245; 548/246

[58] Field of Search ............ 548/240, 245, 548/246, 247

[56] References Cited

U.S. PATENT DOCUMENTS

| 5,591,461 | 1/1997 | Chan et al. | 548/245 |
| 5,594,021 | 1/1997 | Chan et al. | 548/245 |

OTHER PUBLICATIONS

*cited in specification.

Primary Examiner—Amelia Owens
Attorney, Agent, or Firm—Rockey, Milnamow & Katz, Ltd.

[57] ABSTRACT

A process of preparing an alkali metal salt of a hydrophobic sulfonamide is provided. The process includes the step of dissolving a free sulfonamide in an organic solvent in the presence of a saturated alkali metal salt solution and recovering the formed sulfonamide salt from the organic phase.

11 Claims, No Drawings

PROCESS OF PREPARING ALKALI METAL SALYS OF HYDROPHOBIC SULFONAMIDES

TECHNICAL FIELD OF THE INVENTION

The present invention provides a novel process of preparing alkali metal salts of hydrophobic sulfonamides.

BACKGROUND OF THE INVENTION

The vascular endothelium releases a variety of vasoactive substances, including the endothelium-derived vasoconstrictor peptide, endothelin (ET). Endothelin is a potent twenty-one amino acid peptide vasoconstrictor. It is the most potent vasopressor known and is produced by numerous cell types, including the cells of the endothelium, trachea, kidney and brain.

Three distinct endothelin isopeptides, endothelin-1, endothelin-2 and endothelin-3, that exhibit potent vasoconstrictor activity have been identified. The endothelin peptides exhibit numerous biological activities in vitro and in vivo. Endothelin provokes a strong and sustained vasoconstriction in vivo in rats and in isolated vascular smooth muscle preparations; it also provokes the release of eicosanoids and endothelium-derived relaxing factor (EDRF) from perfused vascular beds. Intravenous administration of endothelin-1 and in vitro addition to vascular and other smooth muscle tissues produce long-lasting pressor effects and contraction, respectively. Endothelin also mediates renin release, stimulates ANP release and induces a positive inotropic action in guinea pig atria. In the lung, endothelin-1 acts as a potent bronchoconstrictor. Endothelin increases renal vascular resistance, decreases renal blood flow, and decreases glomerular filtration rate. It is a potent mitogen for glomerular mesangial cells and invokes the phosphoinoside cascade in such cells.

There are specific high affinity binding sites (dissociation constants in the range of 2 to $6 \times 10^{-10}$M) for the endothelins in the vascular system and in other tissues, including the intestine, heart, lungs, kidneys, spleen, adrenal glands and brain. Endothelin binds and interacts with receptor sites that are distinct from other autonomic receptors and voltage dependent calcium channels. Competitive binding studies indicate that there are multiple classes of receptors with different affinities for the endothelin isopeptides. Two distinct endothelin receptors, designated $ET_A$ and $ET_B$, have been identified and DNA clones encoding each receptor have been isolated.

$ET_A$ receptors appear to be selective for endothelin-1 and are predominant in cardiovascular tissues. $ET_B$ receptors are predominant in non-cardiovascular tissues, including the central nervous system and kidney, and interact with the three endothelin isopeptides. In addition, $ET_A$ receptors occur on vascular smooth muscle, are linked to vasoconstriction and have been associated with cardiovascular, renal and central nervous system diseases; whereas $ET_B$ receptors are located on the vascular endothelium, linked to vasodilation and have been associated with bronchoconstrictive disorders. By virtue of the distribution of receptor types and the differential affinity of each isopeptide for each receptor type, the activity of the endothelin isopeptides varies in different tissues. For example, endothelin-1 inhibits $^{125}$I-labeled endothelin-1 binding in cardiovascular tissues forty to seven hundred times more potently than endothelin-3. $^{125}$I-labeled endothelin-1 binding in non-cardiovascular tissues, such as kidney, adrenal gland, and cerebellum, is inhibited to the same extent by endothelin-1 and endothelin-3, which indicates that $ET_A$ receptors predominate in cardiovascular tissues and $ET_B$ receptors predominate in non-cardiovascular tissues.

Circulating endothelin levels are elevated in certain disease states, including shock, myocardial infarction, vasospastic angina, kidney failure and a variety of connective tissue disorders. In addition, in patients undergoing hemodialysis or kidney transplantation or suffering from cardiogenic shock, myocardial infarction or pulmonary hypertension elevated levels have been observed. Elevated levels of endothelin have also been measured in patients suffering from ischemic heart disease. Circulating and tissue endothelin immunoreactivity is increased more than twofold in patients with advanced atherosclerosis. Increased endothelin immunoreactivity has also been associated with Buerger's disease and Raynaud's phenomenon. Increased circulating endothelin levels were observed in patients who underwent percutaneous transluminal coronary angioplasty (PTCA) and in individuals with pulmonary hypertension.

Because endothelin is associated with certain disease states and is implicated in numerous physiological effects, compounds that can interfere with endothelin-associated activities, such as endothelin-receptor interaction and vasoconstrictor activity, are of interest. Compounds that exhibit endothelin antagonistic activity have been identified. A number of such compounds have also been shown to possess activity in in vivo animal models. Such compounds are considered to be useful for the treatment of hypertension such as peripheral circulatory failure, heart disease such as angina pectoris, cardiomyopathy, arteriosclerosis, myocardial infarction, pulmonary hypertension, vasospasm, congestive heart failure, vascular restenosis, Raynaud's disease, cerebral stroke such as cerebral arterial spasm, cerebral ischemia, late phase cerebral spasm after subarachnoid hemorrhage, asthma, bronchoconstriction, renal failure, particularly post-ischemic renal failure, cyclosporine nephrotoxicity such as acute renal failure, colitis, as well as other inflammatory diseases, endotoxic shock caused by or associated with endothelin, and other diseases in which endothelin has been implicated.

Certain sulfonamides can modulate the interaction of an endothelin peptide with $ET_A$ and/or $ET_B$ receptors. In particular, certain such sulfonamides can act as endothelin peptide agonists with respect to $ET_A$ or $ET_B$ receptors. Exemplary such sulfonamides are hydrophobic and are characterized by substituted or unsubstituted monocyclic or polycyclic aromatic or heteroaromatic sulfonamides, such as benzene sulfonamides, particularly biphenyl sulfonamides, naphthalene sulfonamides, and fused tricyclic ring sulfonamides. Particular sulfonamides have been disclosed to modulate endothelin activity (See, e.g. U.S. Pat. Nos. 5,591, 761 and 5,594,021, the disclosures of which are incorporated herein by reference).

Existing methods for making such sulfonamides are associated with certain shortcomings. For example, certain steps in the synthetic pathway are known to result in dimerization of intermediates with the resultant decrease in yield and purity. Second, because the compounds are hydrophobic, purification is difficult, typically requiring the impractical use of preparative HPLC or column chromatography. Finally, the existing methods are limited to the production of the hydrophobic free sulfonamide, which sulfonamide is difficult to formulate into aqueous based pharmaceutical compositions. Attempts to convert the free sulfonamide to useful salts of alkali metals using metal hydroxides or methoxides may lead to decomposition of the compound.

There continues to be a need in the art for a practical, efficient method for making salts of desired sulfonamides.

BRIEF SUMMARY OF THE INVENTION

In one aspect, the present invention provides a process of making an alkali metal salt of a hydrophobic free sulfonamide. The process includes the steps of dissolving the free sulfonamide in an organic solvent, washing the dissolved free sulfonamide with a saturated solution of a salt of the alkali metal, and recovering the alkali metal salt of the sulfonamide from the organic phase.

A preferred organic solvent is ethyl acetate or THF. Preferred alkali metals are sodium, potassium, calcium or magnesium with sodium being most preferred. In accordance with a preferred embodiment, the process uses saturated sodium bicarbonate or sodium carbonate as the alkali metal salt solution. Sodium bicarbonate is most preferred.

Recovery preferably includes the steps of drying the salt solution in organic solvent, concentrating the salt, crystallizing the salt in one or more organic, non-water miscible solvents and collecting the sulfonamide salt by filtration. Preferred organic, non-water miscible solvents are dichloromethane and ether. The process of the present invention can further include the step of purifying the sulfonamide salt after recovery.

A process of the present invention is particularly useful in making 4-chloro-3-methyl-5-(2-(2-(6-methylbenzo[d][1,3]dioxol-5-yl)acetyl)-3-thienylsulfonamido)isoxazole, sodium salt; $N^2$-(3-cyanomethyl-2,4,6-trimethylphenyl)-3-(4-chloro-3-methyl-5-isoxazolylsulfamoyl)-2-thiophenecarboxamide, sodium salt; $N^2$-(3-acetyloxymethyl-2,4,6-trimethylphenyl)-3-(4-chloro-3-methyl-5-isoxazolylsulfamoyl)-2-thiophenecarboxamide, sodium salt; and $N^2$-(3-hydroxymethyl-2,4,6-trimethylphenyl)-3-(4-chloro-3-methyl-5-isoxazolylsulfamoyl)-2-thiophenecarboxamide, sodium salt.

In another aspect, the present invention provides an alkali metal salt of the sulfonamide prepared by the present process. A preferred such sulfonamide salt is 4-chloro-3-methyl-5-(2-(2-(6-methylbenzo[d][1,3]dioxol-5-yl)acetyl)-3-thienylsulfonamido)isoxazole, sodium salt.

DETAILED DESCRIPTION OF THE INVENTION

The present invention provides a process of making an alkali metal salt of hydrophobic sulfonamide modulators of endothelin activity. More particularly, the invention provides a process of making sodium salts of such sulfonamides. The process includes the steps of dissolving the free sulfonamide in an organic solvent in the presence of a saturated aqueous solution of an alkali metal salt and recovering and purifying the sulfonamide salt.

The sulfonamide to be converted to an alkali metal salt can be made by any process well known in the art (See, e.g., U.S. Pat. Nos. 5,591,761 and 5,594,021, the disclosures of which are incorporated herein by reference). By way of example, $N^2$-methoxy-$N^2$-methyl-3-(4-chloro-3-methyl-5-isoxazolylsulfamoyl)-2-thiophenecarboxamide is reacted with 6-methylbenzo[d][1,3]dioxolyl-5-methyl magnesium chloride in an organic solvent to provide 4-chloro-3-methyl-5-(2-(2-(6-methylbenzo[d][1,3]dioxol-5-yl)acetyl)-3-thienylsulfonamido)isoxazole as a crude product that is purified by preparative HPLC. An alternate method of making that sulfonamide is set forth hereinafter in the Examples. Briefly, that process includes the steps of (a) admixing 5-chloromethyl-6-methylbenzo[d][1,3]dioxole and activated magnesium in tetrahydrofuran to form a Grignard reagent; (b) adding $N^2$-methoxy-$N^2$-methyl-3-(4-chloro-3-methyl-5-isoxazolylsulfamoyl-2-thiophenecarboxamide to the reaction admixture; (c) diluting the mixture from step (b) sequentially with a concentrated inorganic acid and an organic solvent to form an aqueous layer and an organic layer; and (d) drying the organic layer and evaporating the solvent to form a residue.

The salt-forming process of the present invention begins with dissolution of the free sulfonamide in an organic solvent. Organic solvents suitable for use in the present invention are well known in the art. Exemplary and preferred organic solvents are ethyl acetate, methyl t-butyl ether, methylene chloride, THF, ether, acetonitrile, dioxane and chloroform. Ethyl acetate is the most preferred organic solvent.

Formation of the alkali metal salt proceeds by exposing the organic solvent containing the free sulfonamide to a saturated solution of an alkali metal salt. The particular salt used will depend on the desired sulfonamide salt to be formed. Alkali metals suitable for use in the present process are well known in the art and include sodium, potassium, calcium, magnesium and the like. For preparation of a sulfonamide salt useful for a pharmaceutical composition, sodium and calcium are the preferred alkali metals. Sodium is most preferred. Anionic components of the salt are well known in the art and include carbonate, phosphate, bicarbonate, nitrate, hydroxide and the like and combinations thereof. Carbonate, bicarbonate and hydroxide anions are preferred. Bicarbonate is most preferred. The alkali metal salt used to form the sulfonamide salt is in the form of a highly concentrated aqueous solution. It is preferred that saturated solutions be used. Means for making saturated alkali metal salt solutions are well known in the art. The biphasic mixture is agitated by any of a number of methods including shaking, stirring, sonication, etc. After allowing the layers to separate, the aqueous phase is removed.

Recovery of the product from the organic solvent is accomplished using any means well known in the art, such as crystallization and filtration. In one embodiment, the organic solvent containing the sulfonamide salt is washed with a concentrated salt solution, wherein the alkali metal is the same as used for salt formation. Where the alkali metal salt is sodium, exemplary wash solutions are concentrated solutions of sodium chloride (e.g., brine) or sodium bicarbonate. Once the protonated form of the sulfonamide has been converted to the salt form, it is important to use concentrated (>than about 3 percent by weight) salt wash solutions. Surprisingly, the alkali metal sulfonamide salt is more soluble in organic solvents than in saturated alkali metal solutions. Use of a diluted solution of salt (e.g., half-strength brine) or water for washing the organic solvent may cause disproportioning of the product between water and the organic layer, and subsequent loss of material. After washing, the product solution can be dried and concentrated to provide crude product as, for example, a residue. In a preferred embodiment, drying occurs over $Na_2SO_4$ or $MgSO_4$ and concentration occurs in vacuo.

The residue is further recovered and purified using recrystallization. In accordance with this embodiment, the product is dissolved in an organic, non-water miscible solvent. Such solvents are well known in the art. Exemplary and preferred such solvents are ether and halomethanes such as dichloromethane and chloroform. A combination of such solvents can also be used. The crystalline product can be isolated from the organic solvent via filtration. The recovered product can be washed one or more times with the organic, non-water miscible solvent. A detailed description of the making of 4-chloro-3-methyl-5-(2-(2-(6-methylbenzo[d][1, 3]dioxol-5-yl)acetyl)-3-thienylsulfonamido)isoxazole, sodium salt in accordance with the disclosed process can be found hereinafter in the Examples.

The sulfonamide salt formed by a process of the present invention can be converted back to the free sulfonamide form and further purified by this process. The sulfonamide salt is dissolved in an aqueous solvent (e.g., water) and filtered. Preferably, filtration occurs through more than one layer of filter paper. Negative pressure or suction may be needed to complete filtration. In some cases, the large amount of impurities that are not soluble in water (10% or higher) slows down the filtration process. This problem can be avoided by using a larger size of filter during the filtration. Usually there is no problem with filtration if the purity of the crude salt is 90% or higher.

The isolated salt, typically in the form of a turbid solution, is converted to an acid by exposing the salt to a concentrated inorganic acid. Suitable acids include hydrochloric acid (HCl), sulfuric acid ($H_2SO_4$), nitric acid ($H_2NO_3$) and the like. Acidification continues until the pH of the product solution is about 1.5 to about 2.5. Acidification preferably takes place at temperatures below about 10° C. The product can precipitate as a milky, non-filterable material during acidification. The slow, dropwise addition of some extra amount of acid causes the product to form a fine, easy filterable precipitate. The precipitate is filtered off, washed with water until neutral and pressed on the filter to get rid of excess of water. The obtained free acid is typically >95% pure as determined by HPLC. The purified sulfonamide can then be converted to the alkali metal salt by the previously described procedure.

Use of a process of the present invention involves shortened reaction times, and results in a more pure product than is possible with other methods. Direct isolation of the sulfonamide salt may be achieved by mixing the product with concentrated alkali salt solutions and organic solvents. The very surprising key observation is that the sulfonamide salt stays in the organic layer, so long as the aqueous layer is heavily salted rather than the aqueous layer as expected. This permits direct isolation of the salt, which can be further purified by conversion to the free sulfonamide and back to the salt, as well as recrystallization. This discovery is key to synthesizing sulfonamide salts with high purity at large scale.

The Examples that follow illustrate preferred embodiments of the present invention and are not limiting of the specification and claims in any way.

EXAMPLE 1

Preparation of (4-chloro-3-methyl-5-(2-(2-(6-methylbenzo[d][1,3]dioxol-5-yl)acetyl-3-thienylsulfonamido) isoxazole A. Formation of 5-chloromethyl-6-methylbenzo[d][1,3]dioxole To a mixture of methylene chloride (130 L), concentrated HCl (130 L), and tetrabutylammonium bromide (1.61 Kg) was added 5-methylbenzo[d][1,3]dioxole (10 Kg) followed by the slow addition of formaldehyde (14 L, 37 wt % in water). The mixture was stirred overnight. The organic layer was separated, dried with magnesium sulfate and concentrated to an oil. Hexane (180 L) was added and the mixture heated to boiling. The hot hexane solution was decanted from a heavy oily residue and evaporated to give almost pure 5-chloromethyl-6-methylbenzo[d][1,3]dioxole as a white solid. Recrystallization from hexane (50 L) gave 5-chloromethyl-6-methylbenzo[d][1,3]dioxole (80% recovery after recrystallization).

B. Formation of (4-chloro-3-methyl-5-(2-(2-(6-methylbenzo[d][1,3]dioxol-5-yl)acetyl)-3-thienylsulfonamido) isoxazole A portion of a solution of 5-chloromethyl-6-methylbenzo[d][1,3]dioxole (16.8 g, 0.09 mol) in tetrahydrofuran (THF)(120 mL) was added to a well stirred slurry of magnesium powder, (3.3 g, 0.136 g-atom, Alfa, or Johnson-Mathey, −20+100 mesh) in THF (120 mL) at room temperature. The resulting reaction admixture was warmed up to about 40°–45° C. for about 2–3 min, causing the reaction to start. Once the magnesium was activated and the reaction begun, the mixture was cooled and maintained at a temperature below about 8° C. The magnesium can be activated with dibromoethane in place of heat.

A flask containing the reaction mixture was cooled and the remaining solution of 5-chloromethyl-6-methylbenzo[d][1,3]dioxole added dropwise during 1.5 hours while maintaining an internal temperature below 8° C. Temperature control is important: if the Grignard is generated and kept below 8° C., no Wurtz coupling takes place. Longer times at higher temperatures promote the Wurtz coupling pathway. Wurtz coupling can be avoided by using high quality Mg and by keeping the temperature of the Grignard below about 8° C., and stirring vigorously. The reaction works fine at −20° C., so any temperature below 8° C. is acceptable at which the Grignard will form. The color of the reaction mixture turns greenish.

The reaction mixture was stirred for an additional 5 min at 0° C., while $N^2$-methoxy-$N^2$-methyl-3-(4-chloro-3-methyl-5-isoxazolylsulfamoyl)-2-thiophenecarboxamide (6.6 g, 0.018 mol) in anhydrous THF (90 mL) was charged into the addition funnel. The reaction mixture was degassed two times then the solution of $N^2$-methoxy-$N^2$-methyl-3-(4-chloro-3-methyl-5-isoxazolylsulfamoyl)-2-thiophenecarboxamide was added at 0° C. over 5 min. TLC of the reaction mixture (Silica, 12% MeOH/$CH_2Cl_2$) taken immediately after the addition shows no $N^2$-methoxy-$N^2$-methyl-3-(4-chloro-3-methyl-5-isoxazolylsulfamoyl)-2-thiophenecarboxamide.

The reaction mixture was transferred into a flask containing 1N HCl (400 mL, 0.4 mol HCl, ice-bath, stirred), and the mixture stirred for 2 to 4 min, transferred into a separatory funnel and diluted with ethyl acetate (300 mL). The layers were separated after shaking. The water layer was extracted with additional ethyl acetate (150 mL) and the combined organics washed with half-brine. Following separation, THF was removed by drying the organic layer over sodium sulfate and concentrating under reduced pressure at about 39° C.

EXAMPLE 2

Preparation of 4-chloro-3-methyl-5-(2-(2-(6-methylbenzo[d][1,3]dioxol-5-yl)acetyl)-3-thienylsulfonamido)isoxazole, sodium salt The product from Example 1 was then re-dissolved in ethyl acetate and washed with saturated $NaHCO_3$ (5×50 mL) until the washings became colorless. The solution was washed with brine, dried over $Na_2SO_4$ and concentrated in vacuo to give a semicrystalline yellow residue. 100 mL of $CH_2Cl_2$ was added to the solution and the mixture stirred under nitrogen for from 5 to 10 minutes until a fine crystalline product was formed. Ether (150 mL) was added and the mixture stirred for an appropriate time (e.g., 10 min).

The product was isolated by filtration, washed with a mixture of $CH_2Cl_2$/ether (1:2) (30 mL) then with ether (30 mL) and dried under reduced pressure. When prepared in accordance with the specific embodiments set forth above, the title product was produced in a quantity of 7.3 g with a purity of around 85% (HPLC, RP, 40% acetonitrile/water, 0.1% TFA neutralized with ammonia to pH 2.5, isocratic conditions, 1 mL/min).

The salt product from above was dissolved in water (600 mL) at 10° C., the solution stirred for a short period of time (e.g., 3 min) and then filtered through a layer of paper filters (e.g., 3 filters) with suction. In some cases, the large amount of impurities that are not soluble in water (10% or higher) slows down the filtration process extremely. This problem can be avoided by using a larger size filter during the filtration. Usually there is no problem with filtration if the purity of the crude salt is 90% or higher.

The greenish slightly turbid solution obtained from filtration was cooled in an ice bath and acidified to a pH of 2 using an acid such as 4N HCl. When the pH of the solution was 2, the product can precipitate as a milky, non-filterable material. Slow dropwise addition of some extra amount of 4N HCl causes the product to form a fine, easily filterable precipitate. The pale yellow precipitate was filtered off, washed with water until neutral and pressed on the filter to get rid of excess of water). The obtained free acid was typically 95% pure as determined by HPLC.

The free acid form of the product was dissolved in ethyl acetate (about 100 ml), washed with brine (30 mL) to remove water. The dehydrated solution was shaken with cold saturated $NaHCO_3$ solution (2×30 mL), then with brine again, dried over $Na_2SO_4$ and concentrated in vacuo (bath temperature lower than 40° C.) to give a very bright yellow foam. After complete removal of the ethyl acetate from this product, $CH_2Cl_2$ (100 mL) was added and the mixture stirred for 5 to 10 min until the product became crystalline. Ether (150 mL) was added and stirring continued for 10 min longer. The formed solid was isolated by filtration, washed with a mixture of $CH_2Cl_2$/ether (1:2) (30 mL) then with ether (30 mL) and dried under reduced pressure. When purified in this manner, 4-chloro-3-methyl-5-(2-(2-(6-methylbenzo[d][1,3]dioxol-5-yl)acetyl)-3-thienylsulfonamido)isoxazole, sodium salt was obtained in high yield (5.7 g, 68%) with good purity (98.2% pure by HPLC). The product can also be further purified by recrystallization from EtOH/ methyl t-butylether (MTBE) after the above procedure, or in place of the protenation/deprotenation sequence if the initial purity is sufficiently high.

What is claimed is:

1. A process of making an alkali metal salt of a hydrophobic free sulfonamide comprising the steps of:
   (a) dissolving the free sulfonamide in an organic solvent;
   (b) washing the dissolved free sulfonamide with a saturated solution of a salt of the alkali metal; and
   (c) recovering the alkali metal salt of the sulfonamide.

2. The process of claim 1 wherein the organic solvent is ethyl acetate.

3. The process of claim 1 wherein the alkali metal is sodium, potassium, calcium or magnesium.

4. The process of claim 3 wherein the alkali metal is sodium.

5. The process of claim 4 wherein the saturated solution of a salt of the alkali metal is saturated sodium bicarbonate, or sodium carbonate.

6. The process of claim 5 wherein the saturated solution of a salt of the alkali metal is saturated sodium bicarbonate.

7. The process of claim 1 wherein recovering comprises the steps of: drying the product of step (b), concentrating that product, crystallizing the product in one or more organic, non-water miscible solvents and collecting the sulfonamide salt by filtration.

8. The process of claim 7 wherein the organic, non-water miscible solvents are dichloromethane and ether.

9. The process of claim 1 further comprising the step of purifying the sulfonamide salt after recovery.

10. The process of claim 1 wherein the free sulfonamide is 4-chloro-3-methyl-5-(2-(2-(6-methylbenzo[d][1,3]dioxol-5-yl)acetyl)-3-thienylsulfonamido)isoxazole; $N^2$-(3-cyanomethyl-2,4,6-trimethylphenyl)-3-(4-chloro-3-methyl-5-isoxazolylsulfamoyl)-2-thiophenecarboxamide, sodium salt; $N^2$-(3-acetyloxymethyl-2,4,6-trimethylphenyl)- 3-(4-chloro-3-methyl-5-isoxazolylsulfamoyl)-2-thiophenecarboxamide, sodium salt; or $N^2$-(3-hydroxymethyl-2,4,6-trimethylphenyl)-3-(4-chloro-3-methyl-5-isoxazolylsulfamoyl)-2-thiophenecarboxamide, sodium salt.

11. The process of claim 1 wherein the free sulfonamide acid is 4-chloro-3-methyl-5-(2-(2-(6-methylbenzo[d][1,3] dioxol-5-yl)acetyl)-3thienylsulfonamido)isoxazole is made by (a) admixing 5-chloromethyl-6methylbenzo[d][1,3] dioxole and activated magnesium in tetrahydrofuran to form a Grignard reagent; (b) adding $N^2$-methoxy-$N^2$-methyl-3-(4-chloro-3-methyl-5-isoxazolylsulfamoyl)-2-thiophenecarboxamide to the reaction admixture; (c) diluting the mixture from step (b) sequentially with a concentrated inorganic acid and an organic solvent to form an aqueous layer and an organic layer; and (d) drying the organic layer to form a residue that contains the free acid.

* * * * *